United States Patent [19]
Horiuchi et al.

[11] Patent Number: 5,594,544
[45] Date of Patent: Jan. 14, 1997

[54] FLOW TYPE PARTICLE IMAGE ANALYZING METHOD AND APPARATUS

[75] Inventors: Hideyuki Horiuchi, Abiko; Koji Suda, Tokushima; Masaetsu Matsumoto, Sendai, all of Japan

[73] Assignee: Hitachi, Ltd., Japan

[21] Appl. No.: 327,271

[22] Filed: Oct. 21, 1994

[30] Foreign Application Priority Data

Oct. 21, 1993 [JP] Japan .................................. 5-263539

[51] Int. Cl.$^6$ ................................................. G01N 21/05
[52] U.S. Cl. ............................................................ 356/73
[58] Field of Search .................................... 356/72, 73, 39

[56] References Cited

U.S. PATENT DOCUMENTS

| | | | |
|---|---|---|---|
| 4,338,024 | 7/1982 | Bolz | 356/23 |
| 4,393,466 | 7/1983 | Deindoerfer | 364/415 |
| 4,476,231 | 10/1984 | Deindoerfer | 436/534 |
| 4,519,087 | 5/1985 | Deindoerfer | 377/10 |
| 4,612,614 | 9/1986 | Deindoerfer | 364/415 |
| 4,667,335 | 5/1987 | Deindoerfer | 377/10 |
| 4,786,165 | 11/1988 | Yamamoto et al. | 356/39 |
| 5,088,816 | 2/1992 | Tomioka | 356/39 |
| 5,173,740 | 12/1992 | Fukuda et al. | 356/72 |
| 5,247,340 | 9/1993 | Ogino | 356/417 |
| 5,412,466 | 5/1995 | Ogino | 356/39 |

FOREIGN PATENT DOCUMENTS

| | | |
|---|---|---|
| 0466168A2 | 7/1991 | European Pat. Off. . |
| 0508688A2 | 4/1992 | European Pat. Off. . |
| 0556971A2 | 2/1993 | European Pat. Off. . |
| 3146423C2 | 4/1981 | Germany . |
| 3705876A1 | 2/1987 | Germany . |
| 57-500995 | 6/1982 | Japan . |
| 60-38653 | 2/1985 | Japan . |
| 60-501624 | 9/1985 | Japan . |
| 63-94156 | 4/1988 | Japan . |
| 3-105235 | 5/1991 | Japan . |
| 3-41783 | 6/1991 | Japan . |
| 4-309841 | 11/1991 | Japan . |
| 4-72544 | 3/1992 | Japan . |
| 5-26143 | 4/1993 | Japan . |
| WO94/08223 | 4/1994 | WIPO . |

*Primary Examiner*—Richard A. Rosenberger
*Attorney, Agent, or Firm*—Bardehle, Pagenberg, Dost, Altenburg, Frohwitter, Geissler and Partners

[57] ABSTRACT

A flow type particle image analyzing method and apparatus in which high-speed and high-precision image analysis can be achieved with a simple configuration are realized. A flow chamber is structured so that the dimension of the sample fluid in a direction substantially orthogonal to the direction of the light beam remains substantially constant in a direction of flow in an imaging zone. Furthermore, when particles have small diameters, a power for imaging is set to a fixed high value. When particles have large diameters, the thickness of a sample fluid is increased in order to provide a sufficient number of sample particles. Accordingly, no switching operation of an optical systems is required.

13 Claims, 5 Drawing Sheets

FLOW TYPE PARTICLE IMAGE ANALYZING METHOD AND APPARATUS

BACKGROUND OF THE INVENTION

The present invention relates to a flow type particle image analyzing method and apparatus in which a sample fluid containing suspended particles flowing in a flat style continuously and then imaged in order to analyze the particles in the sample fluid. More particularly, this invention relates to a flow type particle image analyzing method and apparatus suitable for analysis of cells or particles contained in blood or urine.

In a conventional analyzation, cells existing in blood or cells or particles existing in urine have been categorized and analyzed by mounting specimens on slides and observing them under a microscope. As far as urine is concerned, since a concentration of particles in urine is low, a sample is centrifuged and condensed using a centrifuge for later observation. In an apparatus for automating these observation and examination work, a slide is smeared with a sample of blood or the like and set in a microscope, a stage in the microscope is automatically scanned over the slide and stopped at locations of the particles in order to produce still images of the particles, and then image processing techniques of characteristic extraction and pattern recognition are used to categorize the particles in the sample.

However, the foregoing procedure requires much time for mounting specimens. Moreover, extra work is required to find out particles while moving the stage of a microscope mechanically and move the particles to an image pickup zone. Achieving this work makes analysis time-consuming and machinery complex.

In an effort to improve examination precision and save labor, a flow type particle image analyzing apparatus using a flow chamber in which a sheathing solution that is a purity solution is used as an outer layer in order to provide a very flat flow of a sample fluid has been disclosed in, for example, JP,A,57-500995, JP,A,63-94156, or JP,A,4-72544.

In the flow type particle image analyzing apparatus, a sample fluid moving in the flow chamber is imaged using, for example, a video camera. Produced still images are then processed in order to categorize or count particles in the sample.

A flow type particle image analyzing apparatus for imaging particles in a sample by changing powers has been described as a particle analyzer in U.S. Pat. No. 5,088,816(JP,A,3-105235) and JP,A,4-309841.

The particle analyzer described in the U.S. Pat. No. 5,088,816 and JP,A,4-309841 comprises a strobe for continuously emitting light that flashes for a short period of time, a diaphragm for adjusting an amount of flashlight from the strobe, a diffuser screen for resolving irregularity in luminous intensity of flashlight, a condenser lens for converging flashlight, a flow chamber positioned in the passage of flashlight and designed to provide a flat flow of a sample fluid while enclosing the sample fluid with a sheathing solution, an objective lens for forming images of particles irradiated by flashlight, a high-power projection lens, a low-power projection lens, a TV camera for shooting images, a means for moving the diffuser screen, a means for varying the size of an aperture stop, and a switching means for switching the high-power and low-power projection lenses.

In the flow chamber, a fluid path for a sample fluid has a cross section that tapers in a direction of flow and expands gradually in a direction substantially orthogonal to a direction in which flashlight travels from the vicinity of an entry of an imaging zone toward an exit thereof. This is intended to control postures of flat particles so that flat surfaces of the flat particles will be substantially orthogonal to flashlight and to produce images representing the characteristics of the particles.

In the foregoing particle analyzer, the projection lenses are switched so that an optimal power will be specified according to the diameters of particles to be measured. Thus, analysis can be undertaken. When the projection lenses are switched, depths of focus are changed. The ratio of a flow rate of a sample fluid flowing into the flow chamber to a flow rate of a sheathing solution flowing thereinto is then modified according to a designated depth of field, whereby the sample fluid is changed in thickness.

To be more specific, when the diameters of particles in a sample to be measured are small (about 10 micrometers), the high-power (for example, power 40) projection lens is selected. A smaller depth of focus is designated accordingly. For a high power, therefore, a sample fluid is made thin.

When the diameters of particles in a sample to be measured are large (about several tens of micrometers), the low-power (for example, power 10) projection lens is selected. A large depth of focus is designated accordingly. For a low power, therefore, a sample fluid is made thick.

SUMMARY OF THE INVENTION

Two measuring modes are executed in case that a sample fluid, such as urine including particles having wide rage in diameters. The two measuring modes are a high power field mode (HPF) and a low power field mode (LPF).

In the high power field mode, the magnifying power of an objective lens is made to be high to magnify a part of a sample fluid and to observe small particles, such as red corpuscles, white corpuscles, bacteria or the like. A large amount of sample fluid to be tested is not required because large number of the small particles exist in the sample fluid relatively.

In the low power field mode, all visual field of shooting area is observed in order to detect the existence of important particles in the sample fluid. The number of important particles is very small. The particles to be measured in the low power field mode are particles, such as columunal kidney tubules or epithelium having large diameters.

As described in the U.S. Pat. No 5,088,816 and JP,A,4-309841, high power and low power optical systems must be included in an analyzing apparatus and must be changed with each other in order to execute the two modes of high power field mode and low power field mode.

For changing powers for measurement, as mentioned above, it is required to exchange lenses using a means for switching projection lenses, to shift a diffuser screen, to vary the size of an aperture stop, and to perform refocusing. This results in the conventional flow type particle image analyzing apparatus that has a complex configuration, operates complicatedly, and is expensive. Moreover, there is a difficulty in speeding up analysis. Much time must be spent for control resulting from a change of powers.

Further, when the optical systems are changed with each other, the intensity of radiation of the image shooting system and the magnifying power of an image are changed, so that the image processes are complicated. Therefore, the particles in the sample fluid cannot be analyzed with high accuracy.

An object of the present invention is to realize a flow type particle image analyzing method and apparatus in which the measuring modes can be changed with each other without changing the magnifying power of an optical system and high-speed and high-precision image analysis can be achieved with a simple construction.

According to the present invention, there is provided a flow type particle image analyzing method in which a sample fluid flow containing suspended particles is enclosed with a purity solution, and a beam is irradiated to the sample fluid, and the particles in the sample fluid are imaged by an imaging means, and produced images are analyzed in order to categorize the particles. Herein, a flow chamber for flowing a sample fluid enclosed with a purity solution is constructed so that a sample fluid's dimension substantially orthogonal to the image beam passing through the sample fluid is substantially constant. The imaging means is set to a fixed certain power for imaging. Produced images are then analyzed in order to categorize the particles.

In the foregoing flow type particle analyzing method, preferably, the ratio of a flow rate of a sample fluid flowing into the flow chamber to a flow rate of the purity solution to be flown thereinto is controlled in order to control the dimension of the sample fluid in the direction in which a beam travels. Thus, a plurality of measurement modes can be designated in association with types of particles to be measured. Imaging is achieved with the same power in any of the plurality of measurement modes.

In the foregoing flow type particle image analyzing method, preferably, the imaging means is set to a power for imaging ranging from power 10 to 100 for imaging.

In a flow type particle image analyzing apparatus, a sample fluid containing suspended particles enclosed with a purity solution, a beam is irradiated to the sample fluid, the particles in the sample fluid are imaged by an imaging means, and produced images are analyzed in order to categorize the particles. The flow type particle image analyzing apparatus comprises a beam generating means for generating a beam to be irradiated to a sample fluid, a flow chamber designed to flow a sample fluid with a purity solution and structured so that a dimension of a flow path for a sample fluid in a direction substantially orthogonal to the direction in which a beam travels remains substantially constant, and an image analyzing means for analyzing images produced with the same power for imaging by the imaging means so as to categorize the particles in the sample fluid.

In a flow type particle image analyzing apparatus, a sample fluid containing suspended particles enclosed with a purity solution, a beam is irradiated to the sample fluid, the particles in the sample fluid are imaged by an imaging means, and produced images are analyzed in order to categorize the particles. The flow type particle image analyzing apparatus comprises a beam generating means for generating a beam to be irradiated to the sample fluid, a flow chamber designed to flow a sample fluid enclosed with a purity solution and structured so that a dimension of a flow path for a sample fluid in a direction substantially orthogonal to the direction in which a beam travels remains substantially constant, a particle detecting means for detecting whether or not particles are present in a given area upstream of the particle imaging zone in the flow chamber, a beam generation control means for driving the beam generating means according to a detected signal provided by the particle detecting means, and an image analyzing means for analyzing images that are produced with the same power for imaging by the imaging means so as to categorize the particles in the sample fluid.

Preferably, the foregoing flow type particle image analyzing apparatus further comprises a flow channel control means that controls the ratio of a flow rate of a sample fluid to be flown into the flow chamber to a flow rate of a purity solution to be flown thereinto so as to control the dimension of the sample fluid in the direction in which a beam travels, and thus enables designation of a plurality of measurement modes in association with types of particles to be measured.

In the foregoing flow type particle image analyzing apparatus, preferably, the imaging means is set to a power for imaging ranging from power 10 to 100 for imaging.

In the foregoing flow type particle image analyzing apparatus, preferably, different kinds of particle recognition logic are implemented in association with the plurality of measurement modes in the particle detecting means.

In the foregoing flow type particle image analyzing apparatus, preferably, the image analyzing means executes image processing and particle categorization, which are based on the same logic defining particle categorization, in any of the plurality of measurement modes.

The particles may be living cells, hemocyte in blood, or sediments in urine.

Image analysis may be achieved with a power for imaging held unchanged by differentiating the dimension of a sample, in the direction in which a beam travels, among types of samples. A plurality of measurement modes are available, whereby values representing the dimension of a sample in the direction in which a beam travels are associated with types of particles. When particles to be measured have small diameters, a dimension of a sample fluid in the direction in which a beam travels is decreased. When particles to be measured have large diameters, the dimension of the sample fluid in the direction in which a beam travels is increased. In this case, the dimension of the sample fluid in the direction in which a beam travels has a larger value than the depth of field. However, since the particles to be measured have large diameters, measurement precision will not be affected adversely.

When types of particles to be measured are changed, a signal is sent from the image analyzing means to the flow channel control means so that the ratio of a flow rate of a purity solution to a flow rate of a sample fluid is modified in order to change the dimension of the sample fluid in the flow chamber in the direction in which a beam travels.

With the modification of the flow rate ratio, the flow velocity of the sample fluid varies. The beam generation control means controls commencement of driving the beam generating means according to the varying flow velocity of the sample fluid.

Different kinds of particle recognition logic are implemented in association with the respective measurement modes in the particle detecting means. Particles are therefore detected according to the particle recognition logic that defines a procedure of recognizing presence or absence of particles and is optimal for any of the plurality of measurement modes.

When measurement modes are changed, the same characteristic extraction and particle identification techniques are employed in the image analyzing means.

DETAILED DESCRIPTION OF THE PREFERRED EMBODIMENTS

An embodiment of the present invention will be described in conjunction with FIGS. 1 to 5.

Figure 1:
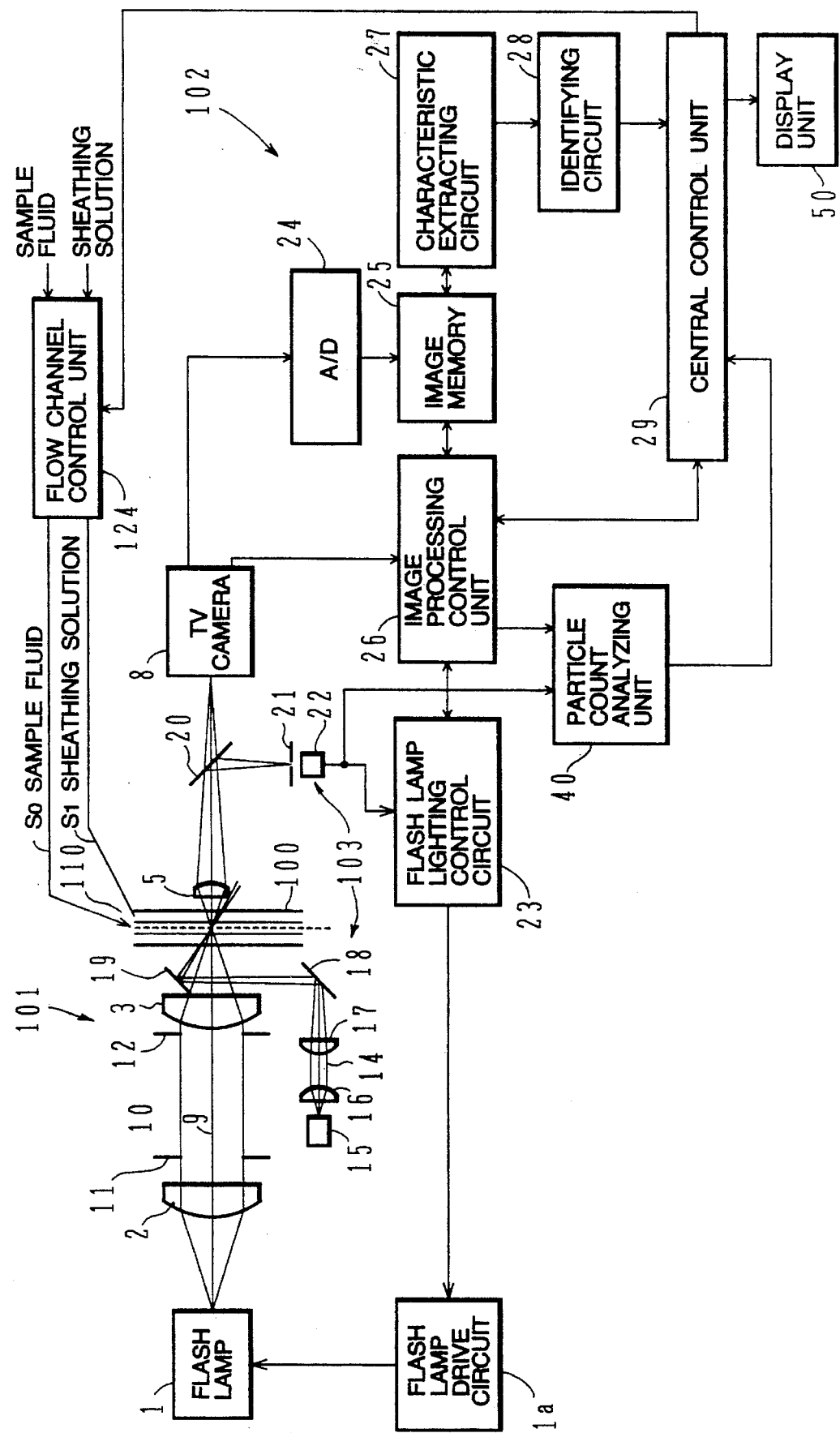
FIG. 1 shows an overall configuration of a flow type particle image analyzing apparatus of an embodiment of the present invention.

FIG. 1 shows an overall configuration of a flow type particle image analyzing apparatus of an embodiment of the present invention.

In FIG. 1, the flow type particle image analyzing apparatus comprises a flow chamber 100, an image pickup 101, a particle analyzer 102, a particle detector 103, and a flow channel control unit 124.

The image pickup 101 includes a flash lamp drive circuit 1a, a flash lamp 1, a field lens 2, a field stop 11, an aperture stop 12, a microscopic condenser lens 3, a microscopic objective lens 5 (which is shared with the particle detector 103), and a TV camera 8. The particle analyzer 102 includes an A/D converter 24, an image memory 25, an image processing control circuit 26, a characteristic extracting circuit 27, an identifying circuit 28, a particle count analyzing unit 40, and a central control unit 29.

Figure 2:
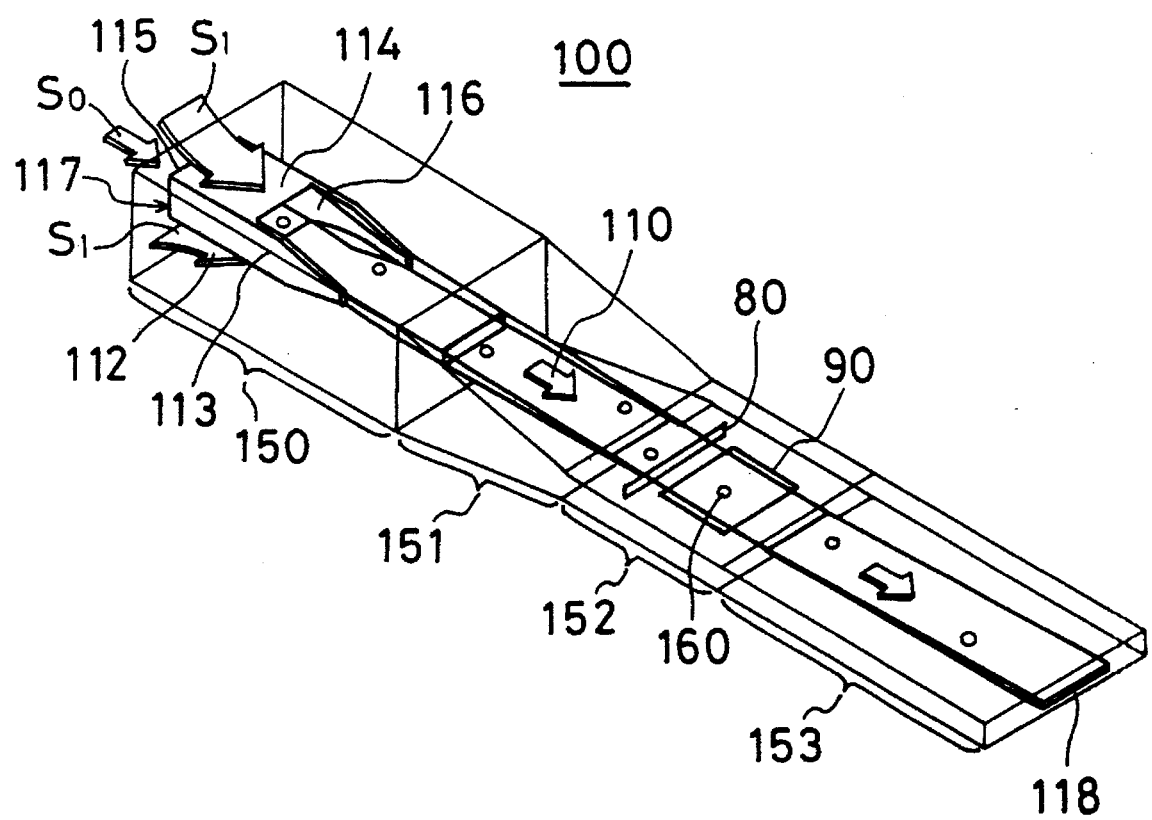
FIG. 2 is an oblique view showing a structure of a flow chamber in the embodiment of the present invention.

The flow chamber 100 includes, as shown in FIG. 2, a parallel flow path 150, a tapering flow path 151, a measurement flow path 152, and a parallel flow path 153. The flow chamber 100 is usually made of a glass.

The parallel flow path 150 extends from an entry 117 to an entry of the tapering flow path 151 and has a square cross section perpendicularly to a direction in which a sample fluid S0 flows. A nozzle 114 is extending from the entry 117 of the parallel flow path 150.

The nozzle 114 has a rectangular cross section whose short sides define the thickness thereof and are oriented in a direction substantially identical to a direction in which flashlight to be described later travels, and whose long sides define the width thereof and are oriented in a direction orthogonal to the direction of the thickness and a direction in which fluid flows. An intersection between diagonal lines of the rectangle is aligned with an intersection between diagonal lines of the square of a cross section of the entry 117 of the parallel flow path 150. Herein, the rectangle is included in the square. The inside of the nozzle 114 serves as a path for the sample fluid S0, and the outside thereof serves as a path for a sheathing solution S1.

The rectangular cross section of the nozzle 114 faces in the direction in which the sample fluid S0 flows and remains unchanged up to a nozzle exit 116. Sample guides 113 for stabilizing the width of the flow of the sample fluid S0 are formed at the nozzle exit 116. The sample guides 113 are a pair of plate members opposed to each other with the flow of the sample fluid S0 between them. The sample guides 113 extend from the nozzle exit 116 up to around the middle of the parallel flow path 150.

The tapering flow path 151 extends from the exit of the parallel flow path 150 to an entry of the measurement flow path 152 and has a square cross section. The width of the tapering flow path 151 does not change but the thickness thereof diminishes gradually toward the measurement flow path 152.

The measurement flow path 152 extends from the entry of the tapering flow path 151 to an entry of the parallel flow path 153 and has the same square cross section as the tapering flow path 151. A particle detecting zone 80 and an imaging zone 90 are formed in the center of the measurement flow path 152.

The particle detecting zone 80 is an elongated area extending along the width of the measurement flow path 152 and having a length that has the same value as the width of the sample fluid S0. The imaging zone 90 is located downstream of the particle detecting zone 80 and shaped like a square each side of which has a length of substantially the same value as the width of the sample fluid S0.

The parallel flow path 153 extends from the exit of the measurement flow path 152 to an exit 118 of the flow chamber 100 and has a square cross section. The width and thickness of the parallel flow path 153 are substantially constant.

Figure 3:
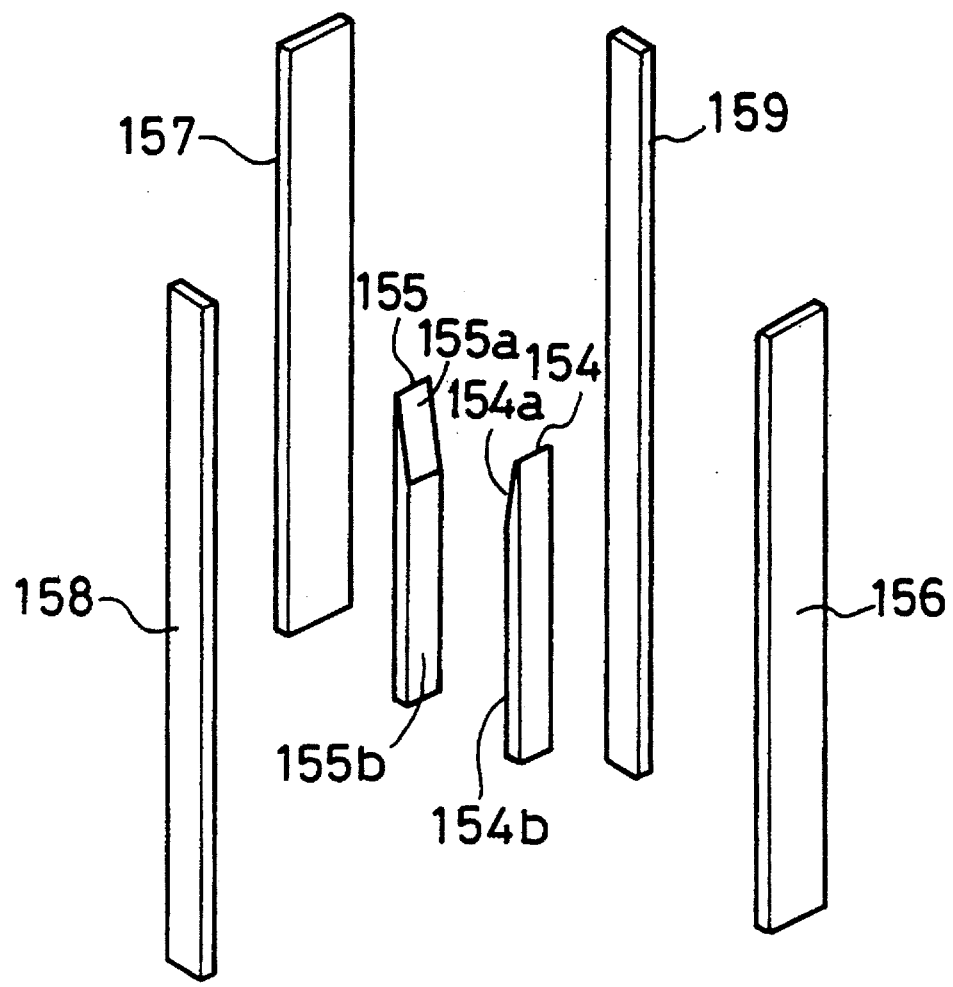
FIG. 3 is an exploded oblique view showing part of the flow chamber shown in FIG. 2.

FIG. 3 is an exploded oblique view showing side plates 156 to 159 serving as side surfaces of the flow chamber 100, and tapered plates 154 and 155 defining the tapering flow path 151. For brevity's sake, these tapered plates 154 and 155, and side plates 156 to 159 are not illustrated in detail in FIG. 2.

The tapered plates 154 and 155 have inclined sections 154a and 155a and parallel sections 154b and 155b. The tapered plates 154 and 155 are disposed so that the inclined sections 154a and 155a are opposed to each other and bounding on the parallel flow path 150, and so that the parallel sections 154b and 155b are continued on the parallel flow path 153. The inclined sections 154a and 155a define the tapering flow path. The parallel sections 154b and 155b define the measurement flow path 152 and parallel flow path 153.

In conformity with the inclined sections 154a and 155a of the tapered plates 154 and 155, the thickness of a flow path for a sample fluid diminishes gradually toward the measurement flow path 152.

Next, the flowage of the sample fluid S0 containing suspended particles and sheathing solution S1 within the flow chamber 100 will be described.

The sample fluid S0 containing suspended particles 160 flows into the parallel flow path 150 through the entry 115 for the sample fluid S0, while the sheathing solution S1 flows thereinto through the entry 117. The sample fluid S0 and sheathing solution S1 flow into the parallel flow path 150 along the outer and inner forms of the nozzle 114 respectively. This results in a two-ply fluid whose inner layer is the sample fluid S0 and whose outer (sheathing) layer is the sheathing solution S1.

The guides 113 of the nozzle 114 restrain the sample fluid S0 from getting turbulent at the nozzle exit 116. The width of a sample fluid can therefore be restricted substantially to the width defined by the guides 113. When the ratio of a flow rate of the sample fluid S0 to that of the sheathing solution S1 is modified, the guides 113 allow the sample fluid S0 to retain the same width but change the thickness.

When fluid flows into the tapering flow path 151, the fluid tapers in width; that is, in a direction in which measurement light travels. Specifically, the fluid forms a super-flat sample flow whose width ranges from 200 to 300 micrometers and whose thickness ranges from several micrometers to several tens of micrometers. Thus, since the fluid is tapered in width alone, postures of flat particles contained in the fluid are controlled so that the flat surfaces of the flat particles are oriented orthogonal to the direction in which the measurement light travels.

When the super-flat sample flow passes through the measurement flow path 152, particles 160 contained in the sample fluid S0 are detected in the particle detecting zone 80 and then imaged in the imaging zone 90.

The super-flat sample flow reaches the exit 118 after passing through the parallel flow path 153.

The flow chamber 100 is designed so that the thickness of the super-flat sample flow in the measurement flow path 152 will be controlled according to the ratio of the flow rate of the sample fluid to the one of the sheathing solution S1. For example, when the flow rate of a sample fluid is constant, if the flow rate of the sheathing solution S1 decreases, the thickness of the super-flat sample flow increases with the width thereof held intact. When the flow rate of the sheathing solution S1 increases, the thickness of the super-flat sample flow decreases with the width thereof held intact.

Figure 4A:
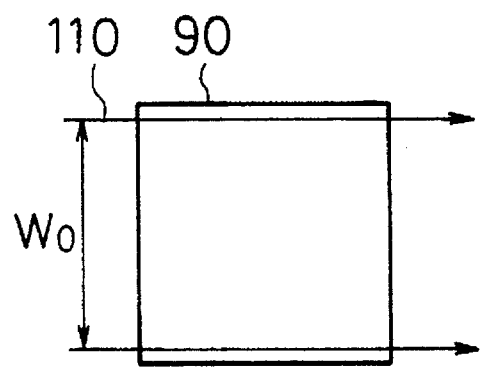
FIGS. 4A, 4B, 4C, and 4D are explanatory views describing the changes in width and thickness of a sample fluid resulting from switching of modes in the embodiment of the present invention.
Figure 4C:
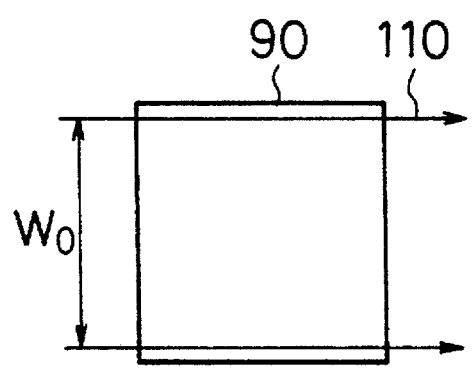
Figure 4B:
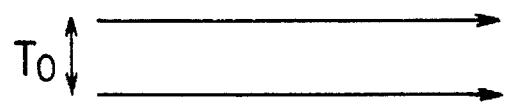

For measuring particles having relatively large diameters (about several tens of micrometers), a measurement mode permitting a relatively thick sample flow is set up. FIG. 4A shows an imaged surface of the sample flow in the measurement mode permitting a thick flow. FIG. 4B shows the thickness (several tens of micrometers) of the super-flat sample flow.

For example, as far as urinary sediments are concerned, even a single particle has different diameters dependent on orientations. Thus, each particle is amorphous and has a maximum diameter of several tens of micrometers. Incidentally, a super-flat sample flow is several tens of micrometers thick. If particles are disposed with the small diameters or thicknesses aligned with the thickness of the sample flow, although the thickness of the sample flow is several tens of micrometers, numerous particles can reside in the sample flow.

Figure 4D:
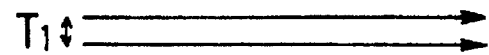

For measuring particles having relatively small diameters (about two to ten and several micrometers); such as, blood cells, a measurement mode permitting a relatively thin sample flow is set up. FIG. 4c shows an imaged surface of the sample flow in the measurement mode permitting a thin flow. FIG. 4D shows the thickness (about several micrometers) of the super-flat sample flow.

As shown in FIGS. 4A to 4D, even when the measurement modes are switched, the width W0 is held constant. The thickness alone changes from T0 (larger value) to T1 (smaller value) or vice versa.

In the example shown in FIG. 1, the optical system is set to a high power (power 20) on a fixed basis and to a small depth of field. When particles having small-diameters are to be measured, a sample flow is made thin so that the thickness of the sample flow is matched with the small depth of field. For measuring particles having large-diameters, the sample flow is made thick in order to provide a sufficient number of samples. In this case, the thickness of the sample flow has a larger value than the depth of field. However, since the particles to be measured have large diameters, although the thicknesses of the particles are mismatched slightly with the depth of field, analytic precision will not be affected adversely.

In FIG. 1, the particle detector 103 includes a semiconductor laser source 15, a collimator lens 16, a cylindrical lens 17, a reflector 18, a micro-reflector 19, a microscopic objective lens 5, a beam splitter 20, a diaphragm 21, a photodetector 22, and a flash lamp lighting control circuit 23. A laser beam emanating from the semiconductor laser source 15 is recomposed into a laser luminous flux 14 made up of parallel rays by the collimator lens 16. The unidirectional portion of the laser luminous flux 14 is converged by the cylindrical lens 17. The converged laser luminous flux is reflected by the reflector 18 and the micro-reflector 19 interposed between the microscopic lens 3 and flow chamber 100, and then irradiated to the particle detecting zone 80 in the flow chamber 100.

The particle detector 103 detects particles on the basis of particle recognition logic defining a procedure of recognizing presence or absence of particles. A plurality of kinds of particle recognition logic are made available. Used for detecting small-diameter particles is recognition logic (algorithm) defining a procedure in which when a detected signal sent from the photodetector 22 becomes level A and has a pulse duration of PA, it is determined that particles have been detected. For detecting large-diameter particles, when a detected signal sent from the photodetector 22 becomes level B that is different from level A used for detecting small-diameter particles, and has a pulse duration of PB that is different from PA, it is determined that the particles have been detected.

Aside from the foregoing recognition logic, also usable is recognition logic defining a procedure in which when a detected signal sent from the photodetector 22 changes waveforms, it is determined that particles have been detected. In this case, different recognition levels are specified in association with magnitudes of diameters of particles to be measured. When a stain is added to a sample fluid, particles may be detected relative to a color level. In this case, different recognition color levels are specified in association with magnitudes of diameters of particles to be measured.

The particle analyzer 102 allows the A/D converter 24 to convert an image data signal provided by the TV camera into a digital signal. Data based on the digital signal is stored at a given address in the image memory 25 under the control of the image processing control circuit 26. The data stored in the image memory 25 is read under the control of the image processing control circuit 26, and fed to the characteristic extracting circuit 27 and identifying circuit 28. Image processing is then carried out. The results of image processing are fed to the central control unit 29. What are fed to the central control unit 29 includes results of particle categorization and characteristic parameters used for identifying particles during the particle categorization. Particle categorization and identification is automatically executed during pattern recognition that is generally adopted. The results of image processing, conditions for measurement, and processed image information are sent from the central control unit 29 to the particle count analyzing unit 40. The particle count analyzing unit 40 checks a particle detected signal sent from the central control unit 29 and photodetector 22 as well as a control signal sent from the image processing control circuit 26 so as to relate detected particles with results of particle categorization on a one-to-one basis, and then finalizes results of categorization and identification concerning the particle images. The results of categorization and identification are returned to the central control unit 29, and output to a display unit 50 if necessary.

Based on the results of measurement, a particulate concentration of the sample and the number of particles in a field of view are calculated. Results of analysis are returned to the central control unit 29.

In response to a signal sent from the central control unit 29, the flow channel control unit 124 controls the ratio of a flow rate of a sample fluid S0 flowing into the flow chamber 100 to that of a sheathing solution S1 flowing thereinto.

Next, the operation of the flow type particle image analyzing apparatus of the embodiment in accordance with the present invention will be described.

In FIG. 1, the sample fluid S0 and sheathing solution S1 flow into the flow chamber 100 shown in FIG. 2 from the upper part of FIG. 2 to the lower part thereof at a high speed without causing a turbulent flow. Flat surfaces of flat particles are oriented substantially perpendicularly to an optical axis 9 of flashlight 10. A laser beam emanating from the semiconductor laser source 15 passes through the collimator lens 16 so as to become a laser luminous flux 14. The laser luminous flux 14 is irradiated to the flow chamber 200 via the cylindrical lens 17, and reflectors 18 and 19. The laser luminous flux passing through the flow chamber 200 is reflected by the beam splitter 20 via the microscopic objective lens 5, and irradiated to the photodetector 22 via the diaphragm 21.

When particles in the sample fluid S0 reach a position in the flow chamber 100 at which the laser luminous flux travels, or in other words, when the particles enter the particle detecting zone, the photodetector 22 transmits a detected signal to the particle count analyzing unit 40 and flash lamp lighting control circuit 23. In response to the detected signal, the flash lamp lighting control circuit 23 lights the flash lamp 1 using the flash lamp drive circuit 1a. The flashlight 10 emanating from the flash lamp 1 is transmitted by the lens 2, and irradiated to the particles residing in the imaging zone 90 in the flow chamber 100 via the field stop 11, aperture stop 12, and microscopic condenser lens 3. Images of the irradiated particles are sent to the TV camera 8 via the microscopic objective lens 5. Based on the information provided by the TV camera 8, the image processing control circuit 26 supplies a command signal to the image memory 25 and particle count analyzing unit 40. Image information provided by the TV camera 8 is supplied to the image memory 25 via the A/D converter 24. The image information is then supplied from the image memory 25 to the characteristic extracting circuit 27. Herein, characteristic information concerning outlines of particles is extracted from the image information, and then supplied to the identifying circuit 28. The identifying circuit 28 identifies types of particles. The results of identification are sent to the central control unit 29.

The central control unit 29 controls the operations of the particle count analyzing unit 40 and image processing control unit 26, and displays processed images on the display unit 50.

The central control unit 29 supplies a control signal to the flow channel control unit 124, and thus allows the flow channel control unit 124 to modify the ratio of a flow rate of the sheathing solution S1 to the one of the sample fluid S0 so that the thickness of the sample fluid S0 in the flow chamber 100 is changed with the width thereof held unchanged.

As mentioned above, according to an embodiment of the present invention, the optical system is set to a high power on a fixed basis. When particles to be measured have small diameters, the thickness of the sample fluid S0 is decreased so that it is matched with a depth of field. When particles to be measured have large diameters or both small and large diameters, the thickness of the sample fluid S0 is increased in order to provide a sufficient number of samples. For measuring large-diameter particles, the thickness of a sample fluid has a larger value than the depth of field. However, since the particles to be measured have large diameters, measurement precision will not be affected adversely. This results in a flow type particle image analyzing method and apparatus in which high-speed and high-precision image analysis can be achieved without causing an optical system to change powers despite a simple configuration.

Further, according to the embodiment of the present invention, since the width of the sample fluid is constant, the width of the image shooting area can be made to coincide with the width of the sample fluid. Therefore, the sample fluid is prevented from flowing outside of the image shooting area, so that the sample fluid can be used effectively.

The embodiment of the present invention uses the flow chamber 100 in which the width and thickness of a sample fluid are retained substantially constant from the entry to exit of the measurement flow path 152 including the particle detecting zone 80 and imaging zone 90. Owing to this structure, a sample fluid flows less turbulently through the measurement flow path 152. Consequently, a variation in the flow velocity of the sample fluid is minimized. In other words, the flow velocity of the sample fluid flowing from the particle detecting zone 80 to imaging zone 90 varies little.

It is therefore possible that when particles detected in the particle detecting zone 80 enter the imaging zone 90, the flash lamp 1 is lit reliably. If the flow velocity varies greatly, there arises a possibility that before or after particles detected in the particle detecting zone 80 enter the imaging zone 90, the flash lamp 1 is lit. In the embodiment of the present invention, since the flow velocity varies little, when particles reside in the imaging zone 90, the flash lamp 1 is lit reliably. This prevents production of unnecessary image information.

Furthermore, according to the embodiment of the present invention, the width of a sample fluid can be retained substantially constant in the measurement flow path 152. A desired thickness of a sample fluid can be calculated easily, and a calculated thickness can be retained with simple control.

Figure 5:
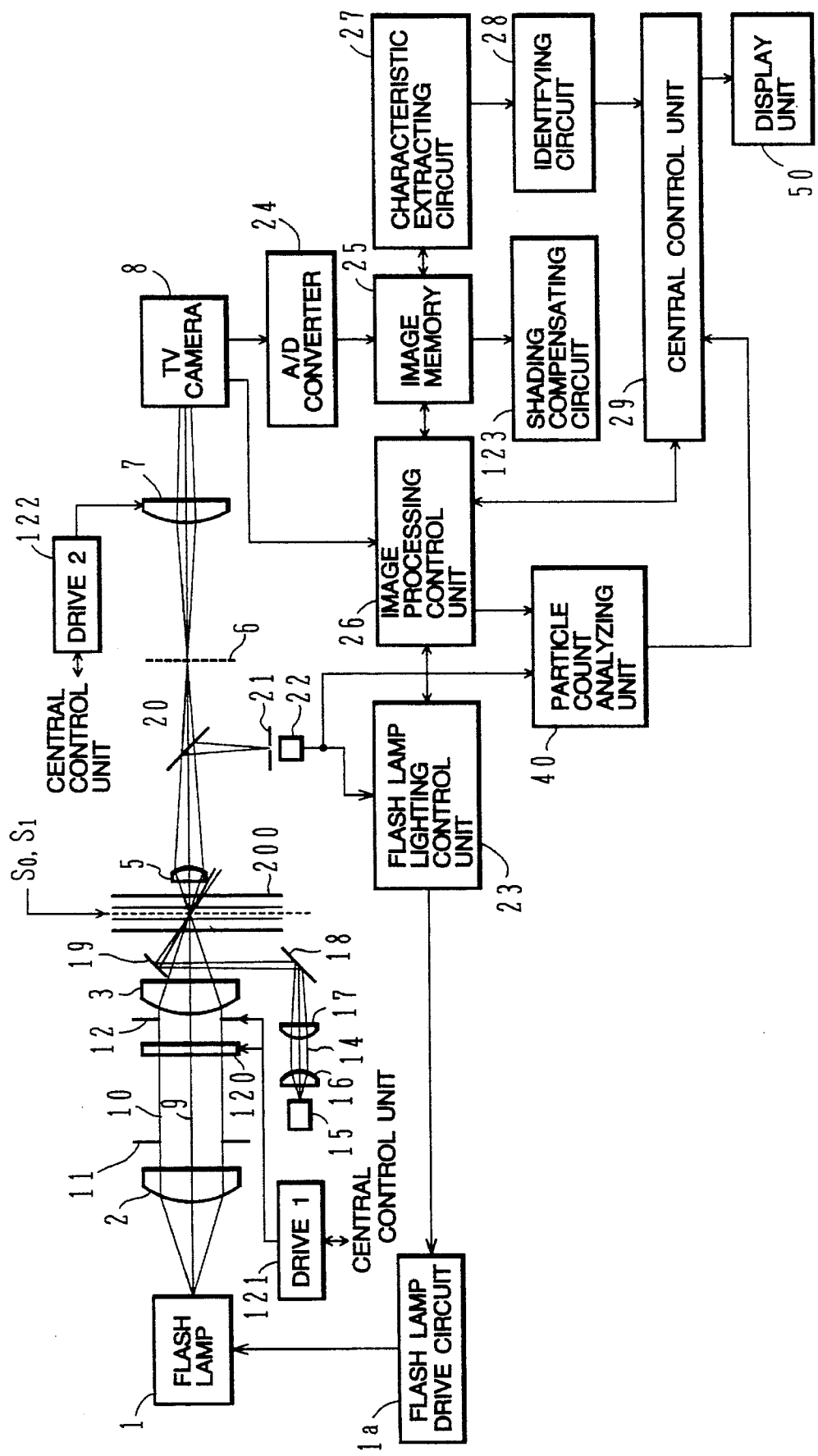
FIG. 5 shows an overall configuration of a flow type particle image analyzing apparatus of a comparable example in accordance with the present invention.

FIG. 5 is a schematic view showing an example of a flow type particle image analyzing apparatus comparable with this embodiment.

In FIG. 5, a sample fluid S0 and a sheathing solution S1 flow through a flow chamber 20 from the upper part of FIG. 5 toward the lower part, thereof. The flow chamber 200 has the same structure as a conventional flow chamber. A flow path for a sample fluid has a cross section that tapers and then expands gradually toward an imaging zone.

A laser beam emanating from a semiconductor laser source 15 passes through a collimator lens 16 so as to be a laser luminous flux 14. The laser luminous flux 14 is irradiated to the flow chamber 200 via a cylindrical lens 17, and reflectors 18 and 19. The laser luminous flux passing through the flow chamber 200 is reflected by a beam splitter 20 via a microscopic objective lens 5, and irradiated to a photodetector 22 via a diaphragm 21.

When particles in the sample fluid S0 reach a position in the flow chamber 200 at which a laser luminous flux travels, the photodetector 22 transmits a detected signal to a particle count analyzing unit 40 and a flash lamp lighting control circuit 23. In response to the detected signal, the flash lamp lighting control circuit 23 lights a flash lamp 1 using a flash lamp drive circuit 1a. Flashlight emanating from the flash lamp 1 is transmitted by a lens 2, and irradiated to particles in the flow chamber 200 via a field stop 11, an ND filter 120 that is driven by a drive 1, an aperture stop 12, and a microscopic condenser lens 3. Images of the irradiated particles are formed at an image-forming position 6 by the microscopic objective lens 5. The images formed at the image-forming position 6 are sent to a TV camera 8 via a projection lens 7 that is driven by a drive 2. Based on information provided by the TV camera 8, an image processing control circuit 26 supplies a command signal to an image memory 25 and the particle count analyzing unit 40. Image information provided by the TV camera 8 is supplied to the image memory 25 via an A/D converter 24, and corrected, if necessary, by a shading compensating circuit 123. Corrected image information is supplied from the image memory 25 to a central control unit 29 via a characteristic extracting circuit 27 and an identifying circuit 28.

The central control unit 29 controls the operations of the particle count analyzing unit 40, image processing control circuit 27, and drives 121 and 122, and displays processed images on a display unit 50.

In the foregoing comparable example, when projection lenses are switched in order to change powers, the ratio of a flow rate of a sample fluid flowing into a flow chamber to the one of a sheathing solution flowing thereinto is modified so that the thickness of the sample fluid is matched with a depth of field dependent on the type of the sample fluid. Thereafter, an ND filter and an aperture stop are moved, the size of the aperture stop is varied, and refocusing is performed.

In a low-power mode, an amount of light surrounding a picked-up image is insufficient. This causes shading in an image signal. A shading compensating circuit is therefore needed to compensate the image signal for shading. In electric shading compensation to be performed for compensating for an insufficient amount of surrounding light, production of data required for compensation and shading compensation based on the data are executed for each image.

In a high-power mode, an amount of light required in the low-power mode is insufficient. A light value control mechanism is therefore needed in order to control an amount of light differently between the high-power and low-power modes.

When powers for imaging are changed, an amount of light on an imaging surface of a TV camera serving as an imaging means is varied and an intensity of an image output signal is fluctuated. The TV camera usually includes a means for controlling a gain. In a flow type particle image analyzing apparatus, when gain control is performed differently between the high-power and low-power modes, optimal images may not be produced. That is to say, since an effective range of gain control has limits and gain-setting requires much time, a high response speed is unavailable. Optimal images may therefore not be produced.

According to the embodiment of the present invention, powers of lenses or amounts of light need not be changed every time measurement modes are switched. This obviates the necessity of an ND filter. Besides, an aperture stop, a projection lens, and a gain control circuit and a shading compensating circuit for a TV camera become unnecessary. This results in a simple configuration, a low price, and fast control. Furthermore, since powers for imaging are not changed with switching of measurement modes, an image pickup area need not be modified. The apparatus can therefore be controlled with ease.

In the aforesaid particle detecting means, a laser luminous flux emanating from a semiconductor laser is used as detection light, and the laser luminous flux scattered by particles is used for analysis. Alternatively, fluorescence or transmitted light emanating from particles may be used for analysis. Also adoptable is a method in which a one-dimensional image sensor is used to detect particles or a method in which a variation in resistance resulting from passage of particles is analyzed to detect the particles.

In the embodiment of the present invention, power 20 is employed as a power for imaging. Alternatively, the present invention can also apply to power 40.

The power for imaging is not limited to powers 20 and 40. The present invention can apply to a power for imaging ranging from power 10 to 100.

The present invention has the advantages below owing to the aforesaid construction.

A flow chamber is structured so that the dimension of the width of a flow path from upstream to downstream in an imaging area is substantially constant, and an imaging power is fixedly set to a high power suitable for small particles, and the thickness of a sample fluid is thicken to obtain sufficient number of large particles when large particles are measured.

Accordingly, this invention can realize a flow type particle image analyzing method and apparatus in which the measuring modes can be changed with each other without changing the magnifying power of an optical system and high-speed and high-precision image analysis can be achieved with a simple construction.

What is claimed is:

1. A flow type particle imaging analyzing apparatus in which a sample fluid containing suspended particles is flown while being closed with a purity solution, a light beam is irradiated to said sample fluid, said particles in said sample fluid are imaged by an imaging means, and produced images are analyzed in order to categorize said particles, said flow type particle imaging analyzing apparatus comprising:

a light beam generating means for generating a beam to be irradiated to said sample fluid;

a flow chamber designed to flow said sample fluid enclosed with said purity solution and structured so that a dimension of a flow path for said sample fluid in a direction substantially orthogonal to the direction of said light beam remains substantially constant;

a particle detecting means for detecting whether or not particles are present in a given zone upstream of said particle imaging zone in said flow chamber;

a beam generation control means for driving said beam generating means according to a detected signal sent from said particle detecting means;

an image analyzing means for analyzing images that are produced with the same power for imaging by said imaging means so as to categorize said particles in said sample fluid; and a flow channel control means that controls the ratio of a flow rate of a sample fluid to be flown into said flow chamber to the one of a purity solution to be flown thereinto so as to control a dimension of said sample fluid is said direction in which a beam travels, and thus enables setting of a plurality of measurement modes in association with types of particles to be measured wherein said plurality of measurement modes has at least one measurement mode in which said image analyzing means has a depth of field smaller than said dimension of said sample fluid in said direction in which said beam travels.

2. A flow type particle image analyzing apparatus according to claim 1, wherein imaging is achieved with said imaging means set to a power for imaging ranging from power 10 to 100.

3. A flow type particle image analyzing apparatus according to claim 1, wherein different kinds of particle recognition logic are implemented in association with said plurality of measurement modes in said particle detecting means.

4. A flow type particle image analyzing apparatus according to claim 1, wherein said image analyzing means executes image processing and particle categorization, which are based on the same logic defining particle categorization, in any of said plurality of measurement modes.

5. A flow type particle image analyzing apparatus according to claim 1, wherein said particles are living cells.

6. A flow type particle image analyzing apparatus according to claim 1, said particles are blood cells.

7. A flow type particle image analyzing apparatus according to claim 1, wherein said particles are urinary sediments.

8. A flow type particle image analyzing method in which a sample fluid containing suspended particles is flown while being enclosed with a purity solution, a light beam is irradiated to the sample fluid, particles in the sample fluid are imaged by an imaging means, and produced images are analyzed in order to categorize the particles, the method comprising:

generating a light beam to be irradiated to the sample fluid;

flowing the sample fluid with the purity solution so that a dimension of a flow path for the sample fluid in a direction substantially orthogonal to the direction of the light beam remains substantially constant;

analyzing images produced with a same power for imaging by the imaging means so as to categorize the particles in the sample fluid; and controlling the ratio of the flow rate of the sample fluid and the flow rate of the purity solution so as to control a dimension of the sample fluid in the direction in which a beam travels, wherein a plurality of measurement modes in association with types of particles to be measured are available and wherein the plurality of measurement modes has at least one mode in which the image analyzing means has a depth of field smaller than the dimension of the sample fluid in the direction in which the beam travels.

9. A flow type particle image analyzing method as claimed in claim 8, wherein said analyzing is of images achieved with an imaging means set to a power between about 10 and about 100.

10. A flow type particle image analyzing method as claimed in claim 8, further comprising detecting whether or not particles are present in a given zone upstream of said generating a light beam.

11. A flow type particle image analyzing method as claimed in claim 10, further comprising controlling said generating according to whether or not particles are detected by said detecting.

12. A flow type particle image analyzing method as claimed in claim 10, wherein different kinds of particle recognition logic are implemented in association with a plurality of measurement modes of said detecting.

13. A flow type particle image analyzing method as claimed in claim 12, wherein said analyzing comprises executing image processing and particle categorization, which are based on the same logic defining particle categorization, in any of the plurality of measurement modes.

* * * * *